United States Patent [19]

Fujiwhara et al.

[11] 4,159,910

[45] Jul. 3, 1979

[54] COLOR PHOTOGRAPHIC MATERIALS CONTAINING COLOR IMAGE FADING INHIBITOR

[75] Inventors: Mitsuto Fujiwhara; Takashi Sasaki; Takashi Uchida, all of Hino, Japan

[73] Assignee: Konishiroku Photo Industry Co., Ltd., Tokyo, Japan

[21] Appl. No.: 822,635

[22] Filed: Aug. 8, 1977

[30] Foreign Application Priority Data

Aug. 9, 1976 [JP] Japan .................................. 51-94667

[51] Int. Cl.$^2$ ................................................. G03C 1/76
[52] U.S. Cl. .......................................... 96/74; 96/56; 96/77; 96/100 R
[58] Field of Search .................... 96/56, 56.5, 74, 100, 96/77

[56] References Cited

U.S. PATENT DOCUMENTS

| | | | |
|---|---|---|---|
| 3,432,300 | 3/1969 | Lestina et al. | 96/56 |
| 3,764,337 | 10/1973 | Arai et al. | 96/100 |
| 3,930,866 | 1/1976 | Oishi et al. | 96/56.5 |
| 4,015,990 | 4/1977 | Ishida et al. | 96/56 |

*Primary Examiner*—J. Travis Brown
*Attorney, Agent, or Firm*—Bierman & Bierman

[57] ABSTRACT

The present invention is related to a color photosensitive material which has a support and a silver halide photosensitive layer and contains a specific compound which acts as a fading inhibitor and also prevents Y-staining.

13 Claims, No Drawings

COLOR PHOTOGRAPHIC MATERIALS CONTAINING COLOR IMAGE FADING INHIBITOR

This invention relates to a color photographic material. More particularly, the invention is concerned with a color photographic material wherein the dye portion and the unexposed portion of the dye image both of which portions are obtained by processing a silver halide color photograhic material are inhibited from discoloring, color-fading, and yellow-staining due to light.

It is known that, in a silver halide color photographic material, a color image may be obtained by using an aromatic primary amine compound (as a developing agent) for development of light-exposed silver halide particles and then reacting the resultant oxidation product of the amine compound with a coupler to form dye images, thereby to obtain color images.

In the above process, a phenol type or naphthol type coupler, a 5-pyrazolone type, pyrazolinobenzimidazole type, pyrazolotriazole type, indazolone type or cyanoacetyl type coupler, and an acylacetamide type or dibenzoylmethane type coupler are ordinarily used to form color images of cyan, magenta and yellow respectively.

As to the dye images thus obtained, it has been desired that they are not discolored, faded, nor yellow-stained even when they are kept at bright places for a long time or reserved in such an atmosphere as at a high temperature and at a high humidity. It is, however, well known that the fastness of color images against, mainly, the ultraviolet or visible rays is still not sufficient and desired to be improved and that the color images may be easily discolored or faded by the exposure to such active rays. In order to remove these defects, there have been heretofore proposed such processes as using a coupler selected from among various couplers of a low fading property, using an ultraviolet absorbing agent to protect color images from the ultraviolet rays, or using a color fading inhibitor to prevent fading due to light.

For example, there have been proposed various processes for improving the light resistance of dye images by using an ultraviolet absorbing agent in a color photograhic material. However, in order to give a sufficient light resistance to dye images by use of an ultraviolet absorbing agent, comparatively a great amount of the absorbing agent is required, so that, in many cases, the coloring of the absorbing agent itself has caused remarkable contamination of dye images. Further, the use of the absorbing agent has no effect to inhibit dye images from fading due to the visible rays and therefore the improvement in light resistance by using an ultraviolet absorbing agent is limited to a certain extent. Furthermore, as a color fading inhibitor having a phenol-type hydroxy group or such a group as producing a phenol-type hydroxy group by hydrolysis, there are proposed those including e.g. bisphenols as disclosed in Japanese Patent Publication Nos. 31,256/73 and 31,625/73, pyrogallol, garlic acid and their esters as disclosed in U.S. Pat. No. 3,069,262, α-tocopherols and their acyl derivatives as disclosed in U.S. Pat. No. 2,360,290 and Japanese Laid-Open-to-Public Patent Publication No. 27,333/76, 6-hydroxychromans as disclosed in U.S. Pat. Nos. 3,432,300 and 3,574,627, and 5-hydroxychroman derivatives as disclosed in U.S. Pat. No. 3,573,050. However, the color fading inhibiting effects by these compounds are not satisfactory. Therefore, in place of these compounds, 6,6'-dihydroxy-2,2'-bisspirochromans or the like have been proposed to be used in Japanese Patent Publication No. 20,977/74.

The compounds of the above publication show certain improvement effects in the light resistance of dye images when compared with the other known compound for the same purpose but such effect is not yet sufficient, because of the following reasons: that, during a long period storage of a color photographic material, said color fading inhibiting effect deteriorates or is lost at insufficient certain point of time; that the spots where unreacted couplers remain, that is, the unexposed portion in ordinary negative photosensitive materials, are changed yellow due to the ultraviolet rays (This phenomenon will be hereinafter called as Y-staining); that said compounds have a low solubility for the solvents used in adding the compounds to a color photographic material; that the compounds are diffused into a high pH treating solution as they have a low diffusion resistance; and, that the compounds are comparatively excellent as to the color fading inhibiting effect on the dye images as obtained from a magenta coupler, while said compounds have no inhibiting effect on the images as obtained from a yellow or cyan coupler or, sometimes, even accelerate the fading of the images.

The object of the present invention is in providing a color photographic material containing an improved color fading inhibitor which has an excellent inhibiting effect on the color fading and the Y-staining and is also excellent in solubility into high boiling point solvents, in dispersion stability and in diffusion resistance, and which inhibitor, at the same time, does not cause any bad effects on other photographic additives nor any disturbance in coloring of a coupler.

After the result of our extensive study, the present inventors have found that the above objects can be accomplished by use of a color photographic material comprising at least one compound represented by the following general formula [1] (The compounds will be hereinafter referred to as the compounds of this invention):

Formula [1]

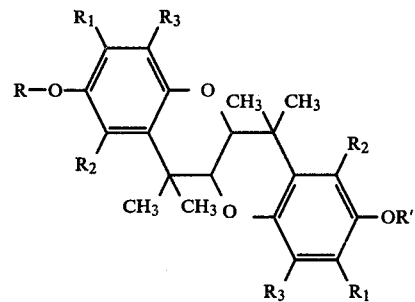

In the formula [I]; $R_1$ represents an alkyl group (e.g. methyl, ethyl, n-propyl, i-propyl, n-butyl, i-amyl, n-octyl, sec-octyl, t-octyl, n-dodecyl or n-octadecyl), an alkenyl group (e.g. allyl, octenyl or oreyl group), an aryl group (e.g. phenyl or naphthyl), an alkoxyl group (e.g. methoxyl, ethoxyl or butoxyl), an alkenoxyl group (e.g. allyloxyl) or an aryloxyl group (e.g. phenyloxyl); $R_2$ and $R_3$ individually represent hydrogen, halogen (e.g. fluorine, chlorine or bromine), an alkyl group (e.g. methyl, ethyl, n-propyl, i-propyl, n-butyl, t-butyl, n-octyl or n-dodecyl), an alkenyl group (e.g. allyl or octenyl) or an alkoxyl group (e.g. methoxyl, ethoxyl, butoxyl or dodecyloxyl); R represents an alkyl group (e.g. methyl, ethyl, n-propyl, i-propyl, n-butyl, t-butyl, n-amyl, i-amyl, n-octyl, n-dodecyl or n-octadecyl), an alkenyl group (e.g. allyl, octenyl or oleyl), a cycloalkyl group (e.g. cyclohexyl), an aryl group (e.g. phenyl), a heterocyclic group (e.g. imidazolyl, furyl, pyridyl or thiazolyl), $R_6CO—$, $R_7SO_2—$ or $R_8NHCO—$; R' is hydrogen, $R_6CO—$, $R_7SO_2—$ or $R_8NHCO—$; $R_6$, $R_7$ and $R_8$ individually represent an alkyl group (e.g. methyl, ethyl, n-propyl, i-propyl, n-butyl, t-butyl, n-octyl or n-dodecyl), an alkenyl group (e.g. allyl, octenyl or octadecenyl), a cycloalkyl group (e.g. cyclopentyl or cyclohexyl), an aryl group (e.g. phenyl, tolyl, or butylphenyl) or a heterocyclic group (e.g. imidazoryl, furyl, pyridyl or thiazolyl); and, the respective above-mentioned groups such as the alkyl group, the alkenyl group, the aryl group, the alkoxy group, the alkenoxy group, the aryloxy group, the cycloalkyl group and the heterocyclic group, include the substituted of which a substituent is such as e.g. halogen (e.g. chlorine or bromine), an alkyl group (e.g. methyl, ethyl, n-propyl, i-propyl, n-butyl, t-butyl, t-octyl or n-dodecyl), an aryl group (e.g. phenyl), an aryloxyl group, a cyano group, an acyloxyl group, a carboalkoxyl group, an acyl group, a sulfamoyl group, hydroxyl, nitro or an amino group. Further, the groups for said substituent include the further substituted of which substituent is appropriately selected from those as mentioned above. And further, when R' represents $R_6CO—$, $R_7SO_2—$ or $R_8NHCO—$, R may be either the same with R' or different from R'. Furthermore, in the general formula [I], the compounds of the following formula [II] are included.

Formula [II]

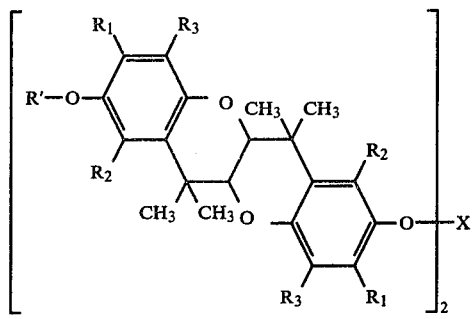

In the formula [II]: R', $R_1$, $R_2$ and $R_3$ individually represent as defined in formula [I] and X represents an alkylene group which includes alkylene, substituted alkylene and an alkylenes which contains in the carbon chain such an intermediate as —O—, —S—, —NA— (A is e.g. hydrogen, a lower alkyl group or an aryl group such as phenyl), —SO— or an arylene group such as phenylene, or a group as shown in the formulae such as

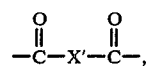

$—SO_2—X'—SO_2—$, or $—CONH—X'—NHCO—$ [In these formulae, X' represents an alkylene group which includes alkylenes which contains, in the carbon chain, such an intermediate as —O—, —S—, —NA— (A is as defined above) or —SO_2—, or an arylene group such as phenylene].

Further, the compounds having general formulae [I] and [II] wherein $R_1$ has an alkyl, alkenyl or aryl group which includes the substituted or unsubstituted and $R_2$ and $R_3$ individually have hydrogen or an alkyl group including the substituted or the unsubstituted (Herein, the substituent for the substituted represents such as mentioned above) are preferred.

Furthermore, particularly useful are those compounds of formulae [I] and [II] wherein $R_1$ has an alkyl group or an aryl group, such as phenyl, which group may be substituted with an alkyl group; $R_2$ and $R_3$ each having hydrogen; R having an alkyl, alkenyl, cycloalkyl, $R_6—CO—$, $R_7SO_2—$ or $R_8NHCO—$ group which includes the substituted of which substituent is phenyl or carboalkoxyl; $R_6$, $R_7$ and $R_8$ each having an alkyl group or an aryl group, such as phenyl, which includes the substituted of which substituent is an alkyl group; and X having an alkylene group or

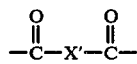

(Herein, X' represents an alkylene group).

In formulae [I] and [II], all the alkyl or alkenyl group are preferably of 1-32 carbon atoms. Especially the alkyl group for R in formula [I] and $R_6$ in formulae [I] and [II] are more preferably of 1-18 carbon atoms, most preferably of 1-8 carbon atoms.

Although the compound of this invention can be prepared by substituting either or both of phenolic hydroxyl groups of 6,6'-hydroxy-2,2'-bisspirochroman with substituents, it has not been heretofore expected that the compound of this invention is excellent in the properties of color-fading inhibition, Y-staining inhibition and solubility into solvents when compared with the conventional color-fading inhibitors.

The representative examples of the compounds of this invention will be shown in the following, but the compounds as used in the present invention is not intended to be limited to such examples:

Exemplified compounds:

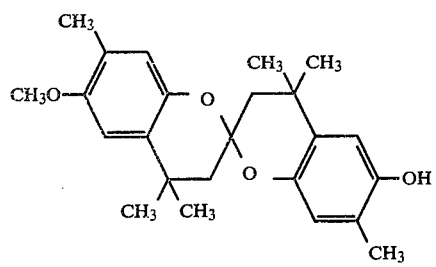

m.p. 151°–3° C.    (1)

-continued
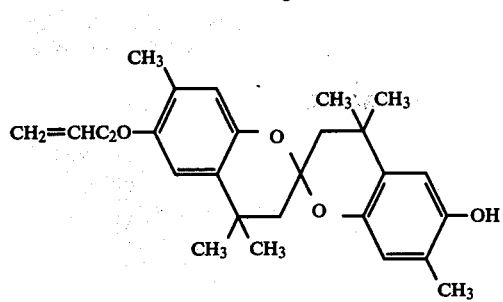
m.p. 123°–5° C.    (2)
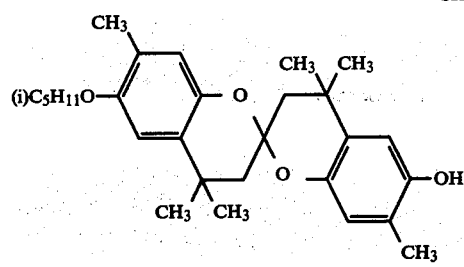
m.p. 145°–6° C.    (3)
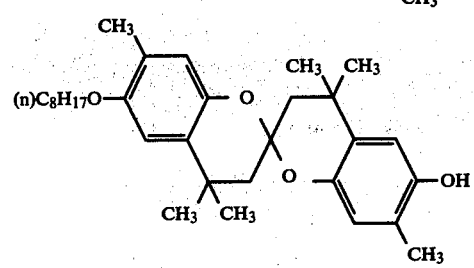
a viscous liquid    (4)
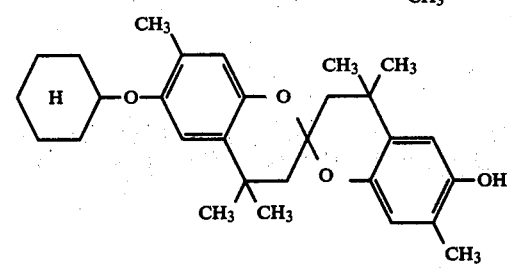
m.p. 190°–4° C.    (5)
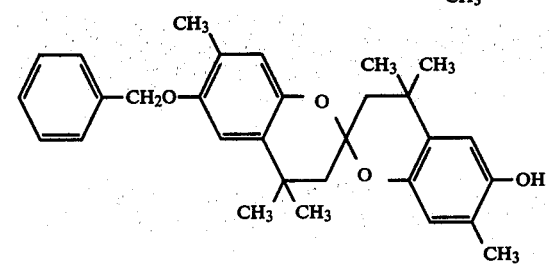
m.p. 147°–8° C.    (6)
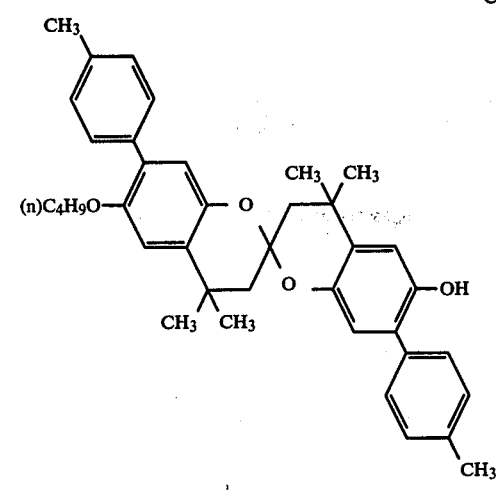
m.p. 230°–2° C.    (7)

-continued
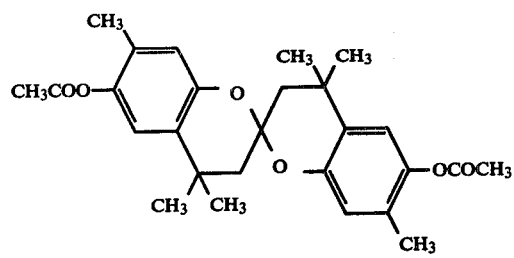 m.p. 206°–8° C. (8)
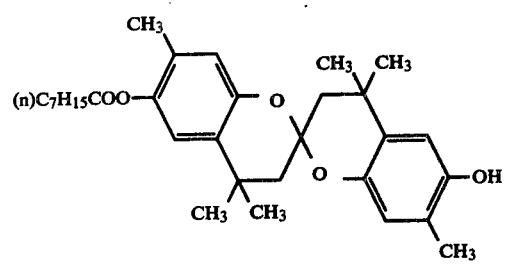 a viscous liquid (9)
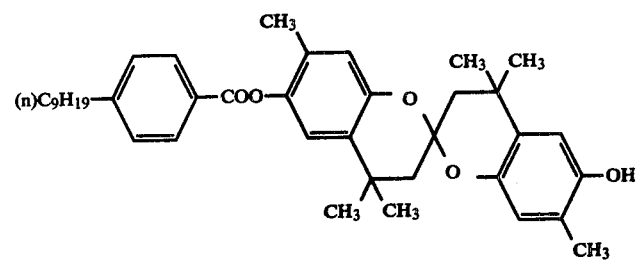 a viscous liquid (10)
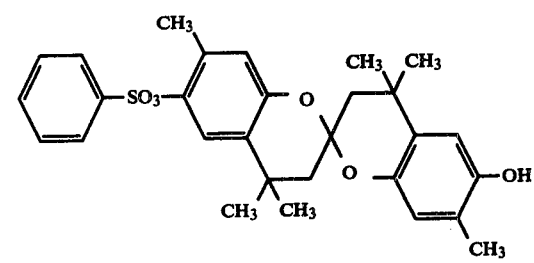 m.p. 215°–8° C. (11)
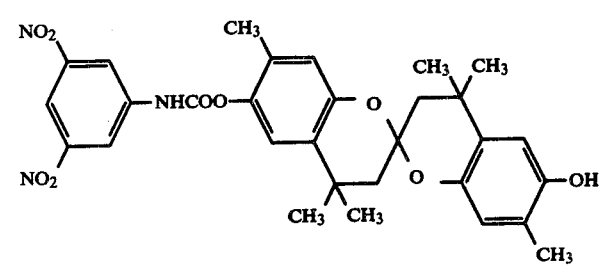 m.p. > 280° C. (12)
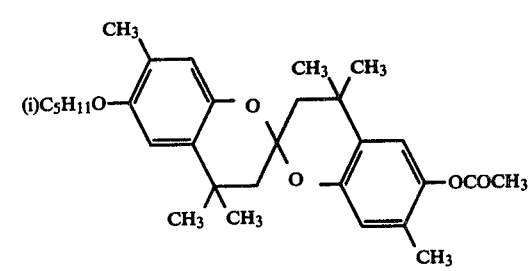 m.p. 150°–1° C. (13)

-continued
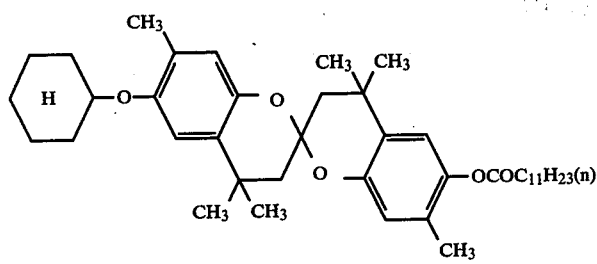
m.p. 154°–6° C. (14)
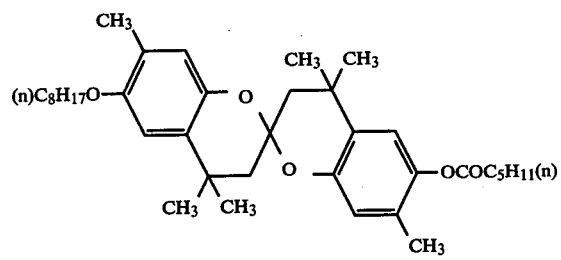
m.p. 132°–4° C. (15)
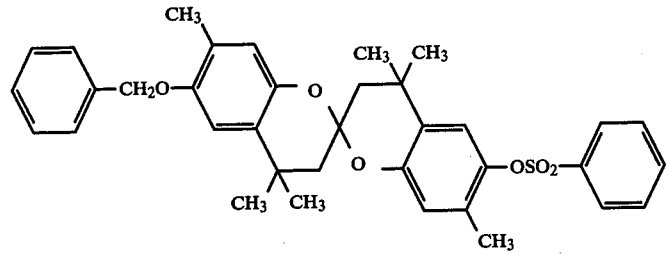
m.p. 165°–7° C. (16)
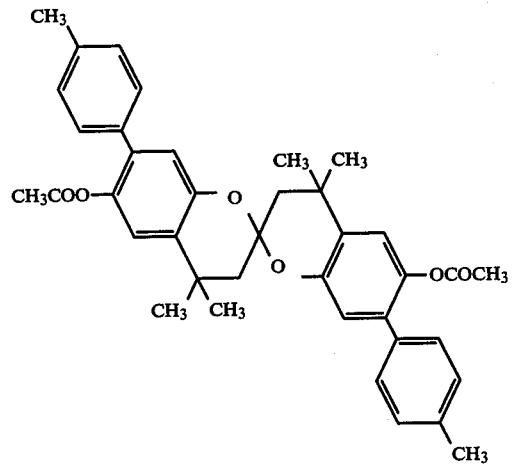
m.p. > 280° C. (17)
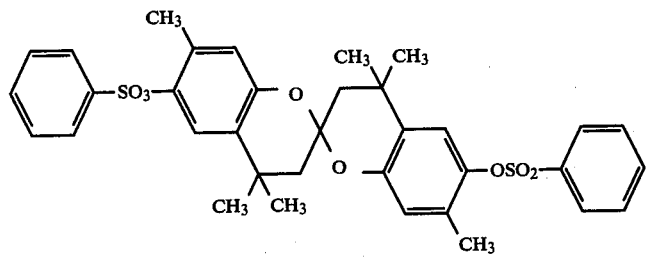
m.p. 198°–200° C. (18)
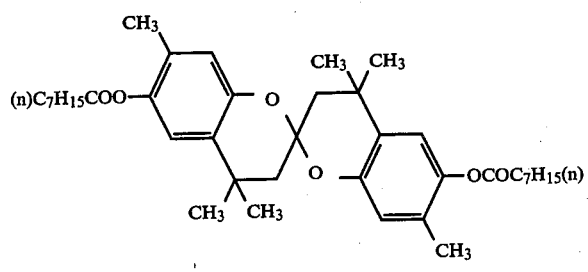
b.p. 230°–240° C./0.02 mmHg (19)

-continued
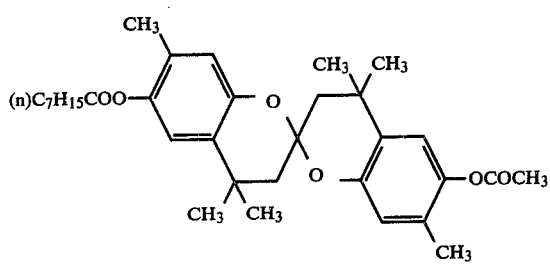
b.p. 172°–180° C./0.001 mmHg    (20)
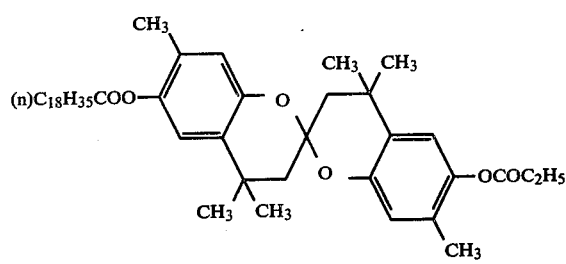
m.p. 30°–40° C.    (21)
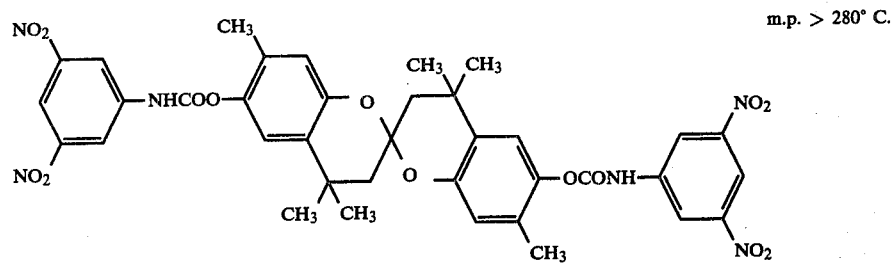
m.p. > 280° C.    (22)
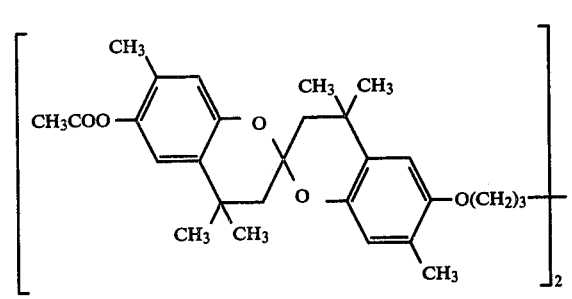
m.p. 147°–150° C.    (23)
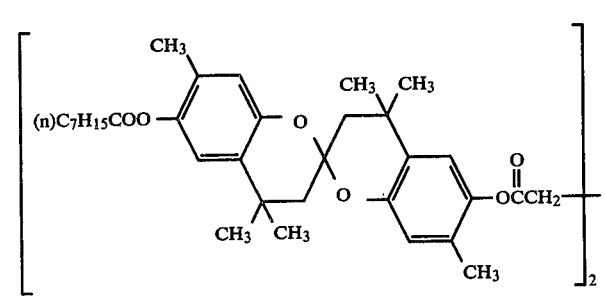
m.p. 40°–45° C.    (24)
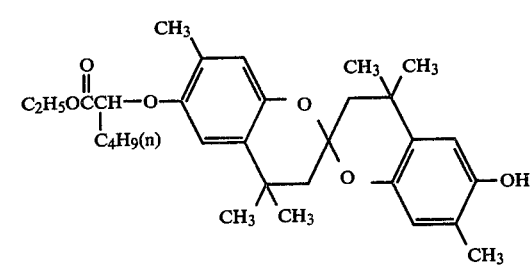
m.p. about 30° C.    (25)

-continued

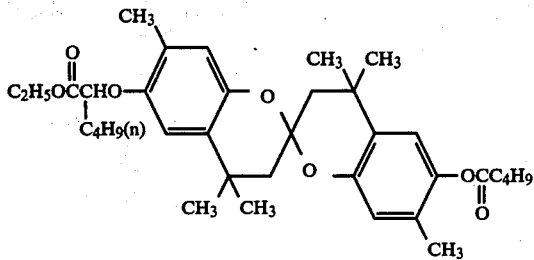

a viscous liquid (26)

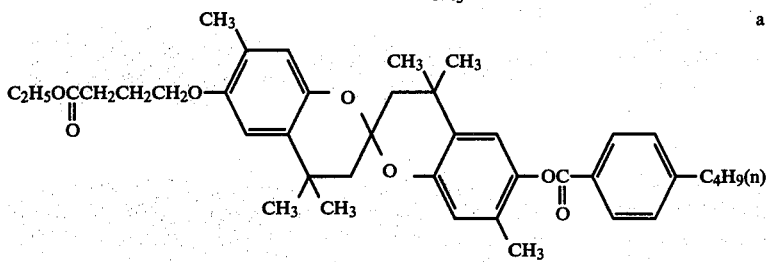

a viscous liquid (27)

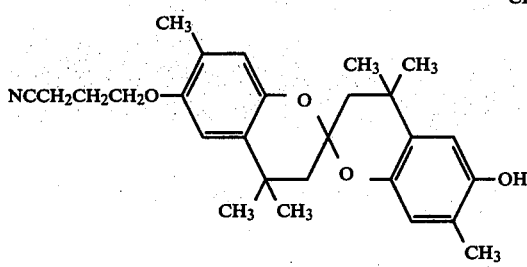

a viscous liquid (28)

The compound of this invention can be obtained by carrying out, according to ordinary processes, the alkylation or acylation of the 6,6'-dihydroxy-4,4,4',4'-tetramethyl-bis-2,2'-spirochroman compound which is prepared in such process as disclosed in U.S. Pat. No. 3,764,337.

Typical examples of the synthetic preparation for the compound of this invention will be illustrated as follows:

Synthetic Preparation 1

Compound (4)

184 g of 6,6'-dihydroxy-7,7'-dimethyl-4,4,4',4'-tetramethyl-bis-2,2'-spirochroman and 96 g of n-octylbromide were dissolved into one liter of dioxan. The resulting solution was incorporated with an aqueous solution of 28 g calcium hydroxide and 100 ml water. Then, heating the resulting solution on an oil bath by reflux was carried out for three hours.

The resulting salt deposited was filtrated and the solvent is removed away. A residual cyrup was dissolved into n-hexane and then washed with an aqueous alkaline solution. In this process, dihydroxyspirochroman as a primary material is transferred to the alkaline aqueous solution. After being washed with water, the solvent was removed away and the residue was washed with added methanol to deposit as a by-product 6,6'-di-n-octyl-7,7'-dimethyl-4,4,4',4'-tetramethylbiss-2,2'-spirochroman. The by-product was filtrated away and methanol was removed away from the resulting thereby to obtain a viscous liquid. Yield of 140 g. Further, the liquid was purified by the column chromatography to obtain a viscous liquid.

The liquid was confirmed as an intended material according to the nuclear magnetic resonance (NMR), the infrared absorption (IR) and the elementary analysis, giving the following data:

Calculated for $C_{31}H_{44}O_4$: C 77.46%, H 9.23%; Found: C 77.34%, H 9.41%.

Synthetic Preparation 2

Compound (13)

45 g 6-hydroxy-7,7'-dimethyl-4,4,4',4'-tetramethyl-6'-i-amyloxy-bis-2,2'-spirochroman of m.p. 145°–146° C. as obtained in the same process as in Synthetic Preparation 1 was added into 15 ml of acetic anhydride. With addition of several drops of concentrated sulfuric acid the exothermic reaction started. After heating for one hour on a water both, the reacted solution was poured into water to filtrate crystals. The crystals were washed with water and recrystalized in 900 ml of methanol. 37 g of the white crystals with m.p. 150°–151° C. is obtained. The NMR, IR and elementary analysis indicated the crystals as an intended substance, as follows:

Calculated for $C_{30}H_{40}O_5$: C 74.97%, H 8.39%; Found: C 75.11%, H 8.26%.

Synthetic Preparation 3

Compounds (9) and (19)

36.8 g of 6,6'-dihydroxy-7,7'-dimethyl-4,4,4',4'-tetramethyl-bis-2,2'-spirochroman was dissolved into 90 ml of an aqueous 10% sodium hydroxide solution and water-cooled. While stirring, 36 g of chrolide caprylate was dipped thereinto. After dipping, the reaction was carried out at a room temperature for one hour. Then, the solution is added with 150 ml of water and subjected to the extraction with ether. The ether layer was washed with an aqueous dilute sodium hydroxide solution to remove an unreacted 6,6'-dihydroxy-7,7'-dimethyl-4,4,4',4'-tetramethyl-bis-2,2'-spirochroman.

After the ether layer was washed with water and dried with anhydrous sodium sulfate, ether was removed away to obtain a cyrup containing compounds (9) and (19) at the ratio of about 1 : 3. Although this substance may be used as such without causing any practical disturbance, the substance was further refined in the following process. The material was refined by the column chromatography to be separated into two kinds of compounds (9) and (19). The latter was furthermore refined by distillation to obtain 37.3 g of a cyrup of m.p. 230°–240° C./0.02 mmHg, which was confirmed as compound (19) by the following data according to the NMR, IR and elementary analysis:

Calculated for $C_{39}H_{56}O_6$: C 75.44%, H 9.09%; Found: C 75.36%. H 9.25%.

The former compound was a liquid too viscous to be distilled and therefore the compound was further subjected to the column chromatography to obtain 11.4 g of crystals. The crystals were confirmed as compound (9) according to the NMR, IR and elementary analysis, as follows:

Calculated for $C_{31}H_{42}O_5$: C 75.27%, H 8.56%; Found: C 75.33%, H 8.74%.

Synthetic Preparation 4

Compound (18)

365 g of 6,6'-dihydroxy-7,7'-dimethyl-4,4,4',4'-tetramethyl-bis-2,2'-spirochroman was dissolved into 600 ml of pyridine. While stirring, 390 g of chloride benzenesulfonate was dripped drown thereinto at a temperature of 30°–35° C. After dripping, the reaction was carried out at a temperature of 50°–55° C. for two hours. Then, the resulting solution was poured into a mixed solution comprising of 780 ml concentrated hydrochloric acid, 1 l. water and 2 l. methanol to deposit crystals. The crystals were washed with methanol and crystalized with a mixed solution comprising of methanol and acetone at the ratio of 1 : 1 to obtain 434 g of white prismatic crystals with m.p. 198°–200° C. The crystals were confirmed as an intended substance according to the NMR, IR and elementary analysis, as follows:

Calculated for $C_{35}H_{36}O_8S_2$: C 64.75%, H 5.55%, S 9.88%; Found: C 65.01%, H 5.53S 10.12%.

While it is preferable for the compound of this invention to be added into a silver halide emulsion layer, it may also be added into other kinds of layers, such as e.g. the layers adjacent to the silver halide emulsion layer.

The compound of this invention is generally oil-soluble, so that it is preferable to dissolve the compound together with a coupler into a high boiling solvent or, if necessary, into a mixed solvent of said solvent and a low boiling solvent, according to such processes as disclosed in U.S. Pat. Nos. 2,322,027, 2,801,170, 2,801,171, 2,272,191 and 2,304,940 and, if desired, in this case, hydroquinone derivatives, ultraviolet absorving agents or conventionally known color facing inhibitors may be used jointly therewith. In the above case, two or more kinds of the compounds of this invention may be also used in mixture. More detailed description concerning the processes of adding the compound of this invention will be made below.

One or more than two kinds of the compounds of this invention and a coupler, if desired, together with a hydroquinone derivative, an ultraviolet absorbing agent or a conventionally known color fading inhibitor, may be dissolved into such high boiling solvent as amides of organic acid, carbamates, esters, ketones or urea derivatives, including particularly e.g. di-n-butylphthalate, tricrezylphosphate, triphenylphosphate, di-isooctylacetate, di-n-butylsebacate, tri-n-hexylphosphate, N,N-diethyl-caprylamidebutyl, n-pentadecylphenyl ether or fluoroparaffin, and if desired, into such low boiling solvent as e.g. ethyl acetate, butyl acetate, butyl propionate, cyclohexanol or cyclohexantetrahydrofuran, (These high boiling solvents and low boiling solvents may be used singly or in combination), may be mixed with an aquous solution containing a hydrophilic binder, such as gelatin, containing an anionic surface active agent like alkylbenzene sulfonic acid or alkylnaphthalene sulfonic acid and/or a nonionic surface active agent like sorbitansesquioleate or sorbitanmonolaurate, may be dispersed and emulsificated by means of a high speed rotating mixer, a coloid mill, a supersonic wave dispersing device or the like, and may be added into a silver halide emulsion.

In the case that a coupler used in the above process is diffusible, it can be possible that the coupler is added into a color developing solution while the compound of this invention and other materials are dispersed and emulsificated into a silver halide emulsion.

The compound of this invention also shows a satisfactory effect even when made present in a silver halide color photographic material after the development.

The added amount of the compound of this invention is not particularly limited because the compound is substantially colorless and therefore does not cause such bad effect as coloring contamination or the like by itself. About 15 g of the compound per mole of the dyes formed by a color development is generally sufficient in amount to be used. However, mainly from economic reasons, a preferably used amount of the compound is between 5 to 300 percents and, in particular, between 10 to 100 percents based on the weight of a coupler in the case of a silver halide color photographic material containing said coupler, and between 10 to 100 g and, in particular, between 15 – 60 g based on one mole of silver halide in the case of a silver halide color photographic material containing no coupler.

As an ultraviolet absorbing agent used in conbination with the compound of this invention, such compounds as e.g. thiazolydone type, benzotriazol type, acrylonitrile type and benzophenone type compounds as disclosed in U.S. Pat. Nos. 2,739,888; 3,004,896; 3,253,921; 3,533,794; 3,692,525; 3,705,805; 3,738,837; 3,754,919; 3,052,636 and 3,707,375 and British Pat. No. 1,321,355 are advantgeous to inhibit color fading due to the shortwave active rays. And, in particular, Tinuvins PS 320, 326, 327 and 328 (The products of Ciba-Geigi & Co.) may be advantageously used singly or in combination for the inhibition as described above.

The typical dye image forming couplers which may be used for a silver halide color photographic material relating to this invention include the compounds as disclosed respectively in the patents as will be mentioned below.

Among typical couplers, yellow dye image forming couplers include benzoylacetanilide type- and pivaloylacetanilide type- yellow dye image forming couplers and divalent type yellow dye image forming couplers having the so-called split-off group, that is, a substituent which may be split-off from the carbon atom in the coupling position of the coupler at the time of a coupling reaction. These couplers are disclosed in, for example, U.S. Pat. Nos. 2,875,057; 3,265,506; 3,664,841;

3,408,194; 3,664,841; 3,408,194; 3,447,928; 3,277,155 and 3,415,652, Japanese Patent Publication No. 13,576/74, and Japanese Laid-Open-to-Public Patent Publication Nos. 29,432/73, 66,834/73, 10,736.74, 122,335/74, 28,834/75 and 132,926/75. And, magenta dye image forming couplers include 5-pyrazolone type-(preferably 3-anilino-5-pyrazolone type-), pyrazolotriazole type-, and indazolone type- magenta dye image forming couplers and divalent magenta dye image forming couplers having a split-off group. These couplers are disclosed in e.g. U.S. Pat. Nos. 2,600,788; 3,062,653; 3,127,269; 3,311,476; 3,419,391; 3,519,429; 3,558,318; 3,684,514 and 3,88,680, Japanese Laid-Open-to-Public Patent Publication Nos. 24,690/75, 134,470/75 and 156,327/75, British Pat. 1,247,493, Belgian Pat. No. 792,525, U.S. Pat. No. 3,061,432, West German Pat. No. 2,156,111, Japanese Patent Publication No. 60,479/71 and Belgian Pat. No. 769,116. Further, cyan dye image forming couplers include phenol type- and naphthol type- cyan dye image forming couplers and divalent type cyan dye image forming couplers having a split-off group. These couplers are disclosed in e.g. U.S. Pat. Nos. 2,423,730; 2,474,293; 2,801,171, 2,895,826; 3,476,563; 3,737,326; 3,758,308 and 3,893,044 and Japanese Laid-Open-to-Public Patent Publications Nos. 37,425/72; 10,135/75; 25,228/75; 112,038/75; 117,422/75 and 130,441/75.

The typical examples of the dye image forming coupler used in this invention have the following formulae:

(Y-1)
α-(4-Carboxyphenoxy)-α-pivalyl-2-chloro-5-[γ-(2,4-di-t-amylphenoxy)butylamide]acetanilide (Y-2)
α-Benzoyl-2-chloro-5-[γ-(2,4-di-t-amylphenoxy)-butylamide]acetanilide (Y-3)
α-Benzoyl-2-chloro-5-[α-(dodecyloxycarbonyl)ethoxycarbonyl]acetanilide (Y-4)
α-(4-Carboxyphenoxy)-α-pivalyl-2-chloro-5-[α-(3-pentadecylphenoxy)butylamide]acetanilide (Y-5)
α-(1-Benzyl-2,4-dioxo-3-imidazolidinyl)-α-pivalyl-2-chloro-5-[γ-(2,4-di-t-amylphenoxy)-butylamide]acetanilide (Y-6)
α-[4-(1-Benzyl-2-phenyl-3,5-diodo-1,2,4-triazolidinyl)]-α-pivalyl-2-chloro-5-[γ-(2,4-di-t-amylphenoxy)butylamide]acetanilide (Y-7)
α-Acetoxy-α-{3-[α-(2,4-di-t-amylphenoxy)-butylamide]benzoyl}-α-methoxyacetanilide (Y-8)
α-{3-[α-(2,4-di-t-Amylphenoxy)butylamide]benzoyl}-2-methoxyacetanilide (Y-9)
α-[4-(4-Benzzyloxyphenylsulfonyl)phenoxy)-α-pivalyl-2-chloro-5-[γ-(2,3-di-t-amylphenoxy)-butylamide]acetanilide (Y-10)
α-Pivalyl-α-(4,5-dichloro-3(2H)-pyridazo-2-yl)-2-chloro-5-[(hexadecyloxycarbonyl)methoxycarbonyl]acetanilide (Y-11)
α-Pivalyl-α-[4-(p-chlorophenyl)-5-oxo-Δ²-tetrazoline-1-yl]-2-chloro-5-[α-(dodecyloxycarbonyl)ethoxycarbonyl]acetanilide (Y-12)
α-(2,4-Dioxo-5,5-dimethyloxazolidine-3-yl)-α-pivalyl-2-chloro-5-[α-(2,4-di-t-amylphenoxy)-butylamide]-acetanilide (Y-13)
α-Pivalyl-α-[4-(1-methyl-2-phenyl-3,5-dioxi-1,2,4-triazolidinyl)]-2-chloro-5-[γ-(2,4-di-t-amylphenoxy)butylamide]acetanilide (Y-14)
α-Pivalyl-α-[4-p-ethylphenyl)-5-oxo-Δ²-tetrazoli-1-yl]-2-chloro-5-[γ-(2,4-di-t-amylphenoxy)-butylamide]acetanilide (M-1)
1-(2,4,6-Trichlorophenyl)-3-[3-(2,4-di-t-amylphenoxyacetamide)benzamide]-5-pyrazolone (M-2)
1-(2,4,6-Trichlorophenyl)-3-(3-dodecylsuccinimidebenzamide)-5-pyrazolone (M-3)
4,4'-Methylenebis{1-(2,4,6-trichlorophenyl)-3-[3-(2,4-di-t-amylphenoxyacetamide)benzamide]-5-pyrazolone (M-4)
1-(2,4,6-Trichlorophenyl)-3-(2-chloro-5-octadecylsuccinimideanilino)-5-pyrazolone (M-5)
1-(2-Chloro-4,6-dimethylphenyl)-3-{3'-[α-(3-pentadecylphenoxy)butylamide]benzamide}-5-pyrazolone (M-6)
1-(2,4,6-Trichlorophenyl)-3-(2-chloro-5-octadecylcarbamoylanilino-5-pyrazolone (M-7)
3-Ethoxy-1-{4-[α-(3-pentadecylphenoxy)-butylamide]phenyl}-5-pyrazolone (M-8)
1-(2,4,6-Trichlorophenyl)-3-(2-chloro-5-tetradecanamideanilino)-5-pyrazolone (M-9)
1-(2,4,6-Trichlorophenyl)-3-{2-chloro-5-[α-(3-t-butyl-4-hydroxyphenoxy)tetradecanamide]anilino}-5-pyrazolone (M-10)
1-(2,4,6-Trichlorophenyl)-3-[3-(2,4-di-t-amylphenoxyacetamide)benzamide]-4-acetoxy-5-pyrazolone (M-11)
1-(2,4,6-Trichlorophenyl)-3-[3-2,4-di-t-amylphenoxyacetamide)benzamide]-4-ethoxycarbonyloxy-5-pyrazolone (M-12)
1-(2,4,6-Trichlorophenyl)-3-[3-(2,4-di-t-amylphenoxyacetamide)benzamide]-4-(4-chlorocinnamoyloxy)-5-pyrazolone (M-13)
4,4'-Benzylidenebis[1-(2,4,6-trichlorophenyl)-3-{2-chloro-5[γ-(2,4-di-t-amylphenoxy)-butylamide]anilino]-5-pyrazoline)

(M-14)
4,4'-Benzylidenebis[1-(2,3,4,5,6-pentachlorophenyl)-3-{2-chloro-5-{γ-(2,4-di-t-amylphenoxy)-butylamide]anilino}-5-pyrazolone]

(M-15)
4,4'-(2-Chloro)benzylidenebis[1-(2,4,6-trichlorophenyl)-3-(2-chloro-5-dodecylsuccimidalino)-5-pyrazolone)

(M-16)
4,4'-Methylenebis[1-(2,4,6-trichlorophenyl)-3-{3-[α-(2,4-di-t-amylphenoxy)butylamide]benzamide}-5-pyrazolone]

(M-17)

1-(2,6-Dichloro-4-methoxyphenyl)-3-(2-methyl-5-acetamidoanilino)-5-pyrazolone (M-18)
1-(2-Chloro-4,6-dimethylphenyl)-3-(2-methyl-5-chloroanilino)-5-pyrazolone (M-19)
1-(2,4,6-Trichlorophenyl)-3-(4-nitroanilino)-5-pyrazolone (M-20)
1-(2,4,6-Trichlorophenyl)-3-(2-chloro-5-octadecenylsuccinimideanilino)-5-pyrazolone (M-21)
1-(2,4,6-Trichlorophenyl)-3-(2-chloro-5-tridecanamidoanilino)-5-pyrazolone (C-1)
1-Hydroxy-N-[δ-(2,4-di-t-amylphenoxy)butyl]-2-naphthoamide (C-2)
2,4-Dichloro-3-methyl-6-(2,4-di-t-amylphenoxyacetamide)phenol (C-3)
2,4-Dichloro-3-methyl-6-[α-(2,4-di-t-amylphenoxy)-butylamide)phenol (C-4)
1-Hydroxy-4-(3-nitrophenylsulfonamide)-N-[δ-(2,4-di-t-amylphenoxy)butyl]-2-naphthoamide (C-5)
1-Hydroxy-4-[(β-methoxyethyl)carbamoyl]methoxy-N-[δ-(2,4-di-t-amylphenoxy)butyl]-2-naphthoamide (C-6)
1-Hydroxy-4-(isopropylcarbamoyl)methoxy-N-dodecyl-2-naphthoamide (C-7)
2-Perfluorobutylamide-5-[α-(2,4-di-t-amylphenoxy)-hexanamide)phenol (C-8)
1-Hydroxy-4-(4-nitrophenylcarbamoyl)oxy-N-[δ-(2,4-di-t-amylphenoxy)butyl)-2-naphthoamide (C-9)
2-(α,α,β,β-Tetrafluoropropyonamide)-5-[α-(2,4-di-t-amylphenoxy)butylamide)phenol (C-10)
1-Hydroxy-N-dodecyl-2-naphthoamide (C-11)
1-Hydroxy-(4-nitro)phenoxy-N-[δ-(2,4-di-t-amylphenoxy)butyl]-2-naphthoamide (C-12)
1-Hydroxy-4-(1-phenyl-5-tetrazolyloxy)-N-[δ-(2,4-di-t-amylphenoxy)butyl]-2-naphthoamide (C-13)
2-(α,α,β,β-Tetrafluoropropyonamide)4-β-chloroethoxy-5-[α-(2,4-di-t-amylphenoxy)butylamido]-phenol (C-14)
2-Chloro-3-methyl-4-ethylcarbamoyl-methoxy-6-[α-(2,4-di-t-amylphenoxy)butylamide]phenol As to each coupler used for a silver halide color photographic material of the present invention, the used amount is generally between 5-50 percents and preferably between 10-30 percents based on one mole of silver halide when the coupler is added into the silver halide color photographic material. When the coupler is added into a developer, the used amount is generally 0.5-3.0 g and preferably 1.0-2.0 g on the basis of one litter of a developing solution. In the above cases, the yellow, magneta and cyan couplers may be used singly or in combination of two or more kinds. When more than two kinds of couplers are used in combination, the sufficient used amount may be the same as specified above.

Further, in combination with the silver halide emulsion may be used hydroquinone derivatives conventionally known as an oxidation inhibitor. The derivatives include for example, such compounds as disclosed in U.S. Pat. Nos. 3,236,893; 3,062,884; 2,816,028; 2,735,765; 2,732,300; 2,728,659; 2,722,566; 2,716,801; 2,704,713; 2,701,197; 2,675,314; 2,418,613, 2,403,721; 2,384,658; 2,360,290 and 2,336,327, British Pats. Nos. 557,750 and 557,802, West Germany Offenlegungschript No. 2,149,789, Japanese Patent Publication No. 54,116/69, Japanese Laid-Open-to-Public Patent Publication No. 2,128/71 and Journal of the Organic Chemistry, Vol. 72, pp. 772-774. Among these hydroquinone derivatives, those having substituted or unsubstituted alkyl as a substituent on the aromatic nucleus thereof are particularly useful and, especially, the preferable compounds include 2,5-di-tert-octyl-hydroquinone, 2,5-di-tert-amyl-hydroquinone and 2,5-di-tert-butyl-hydroquinone.

A silver halide emuslion used for a silver halide color photographic material according to the present invention, comprises, in general, of silver halide particles dispersed in a hydrophilic colloid. Said silver halides include silver chloride, silver bromide, silver iodide, silver chlorobromide, silver iodobromide, silver chloroiodobromide and their mixtures. These silver halides may be prepared by various processes such as an ammonia process, a mixing process, a neutral process, the so-called conversion process and a simultaneous mixing process. The hydrophilic colloids where these silver halides are dispersed are generally geratin and such gelatin derivatives as gelatin phthalate, gelatin malonate or the like. In place of a part or the whole of gelatin or the gelatin derivatives, however there may be used albumin, agar, gum arabic, alginic acid, casein, partlyhydrolyzed cellulose derivative, polyvinyl alcohol, partly-hydrolyzed polyvinylacetate, polyacrylamide, imidized polyacrylamide, polyvinylpyrolidone and copolymers of these vinyl compounds. Further, said silver halide emulsions may be optically sensitized by use of various sensitizing dyes in order to give sensitivity to any desired sensitive light wave length area thereto. As preferable examples of such sensitizing dyes, such cyanine dye, melocyanine dye or combined cyanine dye as disclosed in e.g. U.S. Pats. Nos. 1,939,201; 2,072,908; 2,739,149; 2,945,763; 2,213,995; 2,493,748 and 2,519,001, West German Pat. No. 929,080, British Pat. No. 505,979, may be used singly or in mixture of two or more kinds. Furthermore, if desired, such chemical sensitizers as e.g. thioethers, quarternary ammonium salts and polyalkylene oxides; such stabilizers as e.g. triazoles, tetrazoles, imidazoles, azaindenes, benzothiazoliums, zinc compounds, cadmium compounds and mercaptanes; hardeners including e.g. chromium salts, ziruconium salts, mucochloric acids, and such aldehyde type, triazine type, or polyepoxy compounds, triethylenephosamide type and ethyleneimine type compounds as disclosed in Japanese Patent Publication Nos. 7133/59 and 1,872/71, U.S. Pats. Nos. 3,091,537; 2,736,320; 3,362,827 and 3,325,287 and British Pat. Nos. 686,440 and 1,332,647; such plasticizers as dihydroxyalkanes including e.g. glycerol and 1,5-pentanediol; fluorescent whitening agents; antistatic agents; coating assistants and various other photographic additives may be used singly or in combination of two or more kinds. The silver halide photographic material may be obtained by incorporating, into the silver halide emulsion, the abovedescribed dispersion solution wherein the compound of this invention and other compounds are dispersed and then by coating the resulting emulsion onto such support as a synthetic resin film like those of cellulose acetate, cellulose nitrate, polycarbonate, polyethylenetelephthalate or polystyrene, baryta paper, polyethylene-coated paper sheet or glass plate, while, if desired, forming a halation inhibiting layer, a sub layer, an inter layer, a filter layer, a protective layer or the like between said emulsion layer and said support.

While the silver halide color photographic material in the present invention may be either applied for a coupler-containing silver halide color photographic material (the Agfa type) or a silver halide color photographic material for which a coupler is contained in a developing solution (the Kodachrome type), the photographic material is advantageous particularly of the Agfa type and it is advantageous to carry out the color development by the color developing process after the exposure. The silver halide color photographic material may also be applied for such silver halide color photographic material wherein a coupler and a color developing agent are contained in the same layer and kept away from contact with each other before imagewise exposure but the both are made to come into contact with each other after the exposure, and also for such coupler-containing silver halide color photographic material where a color developing agent is contained in a layer separated from a layer containing a coupler but at the time of permeation of an alkaline processing solution the color developing agent is transferred to come into contact with the coupler. Furthermore, in a diffusion transfer silver halide color photographic material, the compound of the present invention may be added into a light sensitive element and/or an image receiving element of the light sensitive material, and it is particularly advantageous to present the compound in the image receiving element. In the reversal process, a photosensitive material containing the compound of this invention may be developed with a black-white negative developing solution and then exposed to the natural light or processed in a bath containing such fogging agent as a boron compound and further color-developed with an alkaline developing solution containing a color developing agent. In this case a fogging agent can be incorporated into an alkaline developing solution containing a color developing agent, without any disterbance. After the color development, the color photographic material is bleached with a bleaching solution containing as an oxidizing agent, for example, ferricyanilide or a ferric salt of aminocopolycarbonic acid, and then fixed with a fixing solution containing a silver salt solvent such as e.g. thiosulfate to remove both silver images and remaining silver halides and keep dye images remaining. Instead of using a bleaching solution and a fixing solution, a one-bath bleaching-fixing solution containing an oxidizing agent like a ferric salt of aminopolycarbonic acid and a silver salt solvent like thiosulfate may be used to carry out the bleaching-fixation. Further, in combination with the color-development, bleaching, fixation or bleaching-fixation, such processes as the prehardening, neutralization, water-washing, stopping and stabilization may be carried out. Particularly, the process for advantageously developing the silver halide color photographic material of this invention consists, for example, of such steps as follows: Color-developing and, if desired, water washing, bleaching-fixing, water washing, and, if desired, stabilizing and drying. These steps are carried out, for example, not only at a high temperature more than 30° C. but also within a very short period of time. The typical example of the process and the typical examples of compositions of processing solutions to be used in each step in the process are as follows: Processing, Steps (At 30° C.);

| Steps | Processing Time |
|---|---|
| Color-developing | 3 min. 30 sec. |
| Bleaching-fixing | 1 min. 30 sec. |
| Water washing | 2 min. |
| Stabilizing | 1 min. |
| Drying | |
| Composition of Color-Developing Solution; | |
| Benzylalcohol | 5.0 ml |
| Sodium hexametaphosphate | 2.5 g |
| Anhydrous sodium sulfite | 1.9 g |
| Sodium bromide | 1.4 g |
| Potassium bromide | 0.5 g |
| Borax ($Na_2B_4O_7 \cdot 10H_2O$) | 39.1 g |
| N-ethyl-N-$\beta$-methanesulfonamidoethyl-4-aminoanilinesulfate | 50.0 g |

Water is added to make the total one liter and sodium hydroxide is added to adjust the solution at pH 10.30.

| Composition of Bleaching-Fixing Solution; | |
|---|---|
| Iron ammonium ethylenediaminetetracetate | 61.0 g |
| 2-Ammonium ethylenediaminetetracetate | 5.0 g |
| Ammonium thiosulfate | 124.5 g |
| Sodium metadisulfite | 13.3 g |
| Anhydrous sodium sulfite | 2.7 g |
| Water is added to make the total one liter and sodium hydroxide is added to adjust the resultant solution at pH 6.5. | |
| Composition of Stabilizing Solution; | |
| Glacial acetic acid | 20 ml |
| Water | 800 ml |

Sodium acetate is added to adjust the solution at pH 3.5–40 and then water is added to make the total one liter.

Typical color-developing agents particularly advantageously used for color-developing a silver halide color photographic material of the present invention are primary phenylenediamines, aminophenols and the derivatives thereof, including e.g. those as shown in the following: The salts of such inorganic acids as chloric acid or sulfonic acid, or of such organic acids as p-toluenesulfonic acid, of those which include N,N-dimethyl-p-phenylenediamine, N,N-diethyl-p-phenylenediamine, N,N-carbamidemethyl-N-methyl-p-phenylenediamine, N-carbamidemethyl-N-tetrahydrofurfuryl-2-methyl-p-phenylenediamine, N-ethyl-N-carboxymethyl-2-methyl-p-phenylenediamine, N-carbamidemethyl-N-ethyl-2- methyl-p-phenylenediamine, N-ethyl-N-tetrahydrofurfuryl-2-methyl-p-aminophenol, 3-acetylamino-4-aminodimethylanilide, N-ethyl-N:$\beta$-methanesulfonamidoethyl-4-aminoaniline, N-ethyl-N-$\beta$-methanesulfonamidoethyl-3-methyl-4-aminoaniline and N-methyl-N-$\beta$-sulfonethyl-p-phenylenediamine.

A silver halide color photographic material comprising the compound of this invention may also be processed with a color-developing solution containing a primary aromatic amine-type color developing agent and an oxidizing agent which works to subject a metallic silver image to a redox reaction.

In case of using these color-developing solutions, the color developing agent is oxidized by the oxidizing agent and then coupled with a photographic color coupler to form dye images. These color developing solutions are disclosed in, for example, Japanese Laid-Open-to-Public Patent Publication No. 9,729/73 and the preferable oxidizing agents for this purpose are those cobalt complex salts having the coordination number 6. The color photographic process including the use of these color developing solutions is especially effective on the so-called silver-saving type color photographic material which contains a smaller amount of silver than the conventionally known silver halide color photographic materials.

The particularly advantageous cobalt complex salts include those which contains ligand(s) selected from ethylenediamine, diethylenetriamine, triethylenetetramine, amine, nitrate, nitrite, azide, chloride, thiocyanate, isothiocyanate, water and carbonate, and which, at the same time, have (1) at least two ethylenediamine ligands, (2) at least five amine ligands, or (3) at least one triethylenetetramine ligand. The particularly preferable cobalt complex salts include, for example, those of the following formulae:

$[Co(En)_2(N_3)_2]X$; $[Co(En)_2Cl(NCS)]X$; $[Co(En)_2(NH_3)N_3]X$; $[Co(En)_2Cl_2]X$; $[Co(En)_2(SCN)_2]X$; $[Co(En)_2(NCS)_2]X$; and $[Co(NH_3)_6]X$.

In the above formulae: En represents ethylenediamine; X represents at least one anion selected from chloride, bromide, nitrite, nitrate, perchlorate, acetate, carbonate, sulfite, sulfate, hydrochloride, thiocyanate, isothiocyanate and hydroxyl anions. The most preferable complex salts are hexamine salts of cobalt such as e.g. chloride, bromide, sulfite, sulfate, perchlorate, nitrite and acetate. The cobalt complex salt in a color developing solution is generally used within the concentration range of about 0.14 to about 50 g based on one liter of the color developing solution.

It is also useful to process a silver halide color photographic material comprising the compound of this invention according to such a color photographic processing method that after a development is carried out by use of a color developing solution containing a primary aromatic amino type color developing agent, the developped photographic material is made contact with an amplifying bath containing the above-mentioned oxidizing agent such as e.g. a cobalt complex salt having the coordination number 6. In this case, a color developing agent in the color developing solution is preferably such as those capable of being kept in the light sensitive layer and transferred into the amplifying bath. Among preferable oxidizing agents, for this object, additional to the above-mentioned oxidizing agents, such aqueous solution of hydrogen peroxide as disclosed in Japanese Patent Publication No. 16,023/76 is also useful. It is preferable for processing a silver halide color photographic material to make the above-mentioned amplifying solution containing a silver halide developing inhibitor in addition to the oxidizing agent. Thereby, the amplifying step may be carried out under a room light. According to this manner, it is possible to observe the color formation, and therefore to stop the formation at any desired color density. The preferable developing inhibitors may include water-soluble bromide compounds like potassium bromide and the heterocyclic compounds like tetrazol, azaindene and triazol groups containing neither mercaptor nor ionic iodide.

The ordinary concentration of the cobalt complex salt contained in the amplifying solution is between about 0.2 g to about 20 g per liter, preferably between about 1 g to about 15 g per liter. The ordinary concentration of the aqueous solution of hydrogen peroxide is between about 0.01% to 10%, preferably being between 0.5 to 5%. In the case that water-soluble iodide is used as a developing inhibitor, the ordinary amount contained in the amplifying solution is between about 1 g to about 40 g per liter, while a developing inhibitor having a heterocyclic structure is used ordinarily at a concentration between about 0.01g to about 3 g per liter. The amplifying bath is used generally at pH 6 to 14, and preferably at pH 8 to 12.

The amplifying bath may contain, in addition to the above-mentioned developing inhibitor, if desired, a developing accelerator, a stabilizer, a water softener, a thickening agent, an agent for avoiding ununiform treatment, and the like.

Further, the compound of this invention has a sufficient effect in inhibiting color fading of light-sensitive diazol materials.

While the present invention will be illustrated in further detail below with reference to examples, the modes of practice of the invention are not intended to be limited only to these examples.

EXAMPLE 1

A magenta coupler and the compound of this invention both shown in Table 1—1 were dissolved into a solvents shown in the same table. The solution was further added with 120 mg of 2,5-di-t-octylhydroquinone. Then, the resulted solution was added tp 500 cc of an aqueous 5% gelatin solution containing 2.5 g of sodium dodecylbenzenesulfonate. After dispersed by a homogenizer, the obtained dispersion was added to 1,000 cc of green light-sensitive silver chlorobromide (Silver chloride: 40 mol %) emulsion. As a hardener 10 ml of a 2% methanol solution of N,N',N''-triacryloile-6H-S-triazine was added thereto. The mixture thus obtained was coated on a polyethylene-coated paper sheet and dried to obtain light-sensitive silver halide photographic materials (Samples 1-12). Each sample was exposed to light through wedges and processed with in such manner as shown in the before-detailed process. Then, the samples were exposed to irradiation by a xenon fade-o-meter for 50, 100 and 200 hours, respectively. In Table 1-2, both color-fading and Y-stain increase in the unexposed portion of the samples were shown at the ratio of the after-exposure density against the before-exposure density (Unit : %). The measurement was carried out by use of Sakura Color Density Meter Type PD-6 (Product from Konishiroku Photogrhic Industry Co., Ltd.,), using green light to measure color-fading of the dyes and blue light to measure Y-stain.

Table 1 - 1

| No. | Couplers Amount | (g) | Compounds Amount | (g) | High B.P. Solvents Amount | (cc) | Low B.P. Solvents Amount | (cc) |
|---|---|---|---|---|---|---|---|---|
| 1 | (M-1) | 36 | — | — | DBP | 36 | EA | 100 |
| 2 | " | " | (1) | 11 | " | " | " | " |

Table 1 - 1-continued

| No. | Couplers Amount | (g) | Compounds Amount | (g) | High B.P. Solvents Amount | (cc) | Low B.P. Solvents Amount | (cc) |
|---|---|---|---|---|---|---|---|---|
| 3 | " | " | (3) | " | " | " | " | " |
| 4 | " | " | (13) | " | " | " | " | " |
| 5 | (M-3) | 39 | — | — | TCP | 39 | MA | 100 |
| 6 | " | " | (4) | 12 | " | " | " | " |
| 7 | " | " | (15) | " | " | " | " | " |
| 8 | " | " | (26) | " | " | " | " | " |
| 9 | (M-4) | 39 | — | — | DBP / TCP | 19 / 19 | EA | 100 |
| 10 | " | " | (5) | 12 | " | " | " | " |
| 11 | " | " | (14) | " | " | " | " | " |
| 12 | " | " | (25) | " | " | " | " | " |

DBP : Dibutylphthalate
TCP : Trichlezylphosphate
EA : Ethylacetate
MA : Methylacetate
(These abbreviations will be the same hereafter.)

Table 1 - 2

| | Color-fading ratio | | | Y-Stain Increase ratio | | |
|---|---|---|---|---|---|---|
| Exposing Hours | 50 | 100 | 200 | 50 | 100 | 200 |
| Samples | | | | | | |
| 1 | 73 | 51 | 32 | 430 | 926 | 2,500 |
| 2 | 91 | 84 | 65 | 280 | 810 | 1,900 |
| 3 | 93 | 85 | 67 | 300 | 815 | 1,950 |
| 4 | 94 | 88 | 70 | 300 | 805 | 1,930 |
| 5 | 71 | 53 | 35 | 450 | 930 | 2,600 |
| 6 | 92 | 85 | 72 | 340 | 720 | 1,960 |
| 7 | 97 | 92 | 76 | 320 | 660 | 1,650 |
| 8 | 95 | 80 | 73 | 335 | 715 | 1,890 |
| 9 | 92 | 73 | 42 | 520 | 1,200 | 3,200 |
| 10 | 96 | 86 | 80 | 360 | 826 | 2,400 |
| 11 | 100 | 94 | 87 | 310 | 800 | 2,010 |
| 12 | 99 | 90 | 83 | 320 | 815 | 2,260 |
| Controls | | | | | | |
| 1 | 82 | 60 | 43 | 397 | 906 | 2,200 |
| 2 | 87 | 72 | 54 | 395 | 875 | 2,200 |
| 3 | 89 | 75 | 55 | 431 | 865 | 2,120 |
| 4 | 82 | 74 | 50 | 410 | 860 | 2,400 |
| 5 | 89 | 80 | 63 | 370 | 830 | 2,200 |
| 6 | 90 | 82 | 61 | 365 | 820 | 2,240 |
| 7 | 90 | 76 | 58 | 408 | 1,080 | 3,100 |
| 8 | 93 | 82 | 72 | 425 | 925 | 2,800 |
| 9 | 91 | 83 | 75 | 435 | 975 | 2,650 |

In the above table, controls 1-9 were used in such combination of a coupler with a color-fading inhibitor shown in Table 1-3.

Table 1 - 3

| Controls | Couplers Amount (g) | | Conventional Inhibitors Amount (g) | |
|---|---|---|---|---|
| 1 | (M-1) | 36 | (I) | 11 |
| 2 | " | " | (II) | 11 |
| 3 | " | " | (III) | 11 |
| 4 | (M-3) | 39 | (I) | 12 |
| 5 | " | " | (II) | 12 |
| 6 | " | " | (III) | 12 |
| 7 | (M-4) | 39 | (I) | 12 |
| 8 | " | " | (II) | 12 |
| 9 | (M-4) | 39 | (III) | 12 |

In the above table, conventional colorfading inhibitors (I), (II) and (III) are as follows:

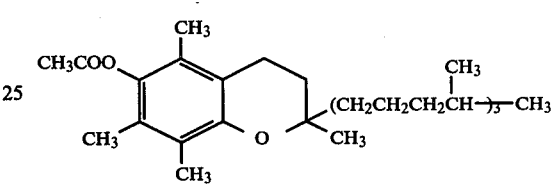

(I)

(Disclosed in Japanese Laid-Open-to-Public Patent Publication No. 27,333/76)

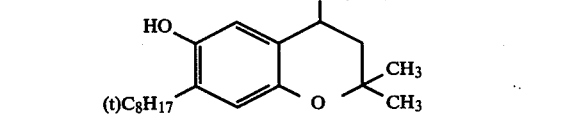

(II)

(Disclosed in U.S. Pat. No. 3,432,300)

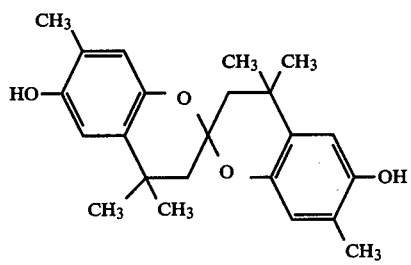

(III)

(Disclosed in U.S. Pat. No. 3,764,337)

As obvious from the results shown in Table 1-2, the compounds of this invention were proved to be excellent in effect of inhibiting the color-fading of a mazenta dye image when compared with those of the conventionally known color-fading inhibitors. Further, it is understood that the compounds of this invention inhibited effectively the Y-stain of the unexposed portion and that such excellent effect remained over a long period of time.

Further, one part of DBP and one part of each of exemplified compounds (1), (3), (4), (5), (14), (15), (25) and (26) were heated to 60° C., to be dissolved and then the solution was left at a room temperature to examine the degree of crystals as deposited. There was no deposition recognized after more than two hours passed. On the other hand, conventionally known color-fading inhibitor (III), for example, did not dissolve into DBP.

EXAMPLE 2

A yellow coupler and the compound of this invention both shown in Table 2-1 were dissolved into the solvents shown in the same table. The solution was further added with 150 mg of 2,5-di-t-octylhydroquinone. Then, the resulted solution was added to 500 cc of an aqueous 5% gelatin solution containing 3.0 g sodium dodecylbenzenesulfonate. After dispersed by a homogenizer, the obtained dispersion was added to 1000 cc of a blue light-sensitive silver chlorobromide (silver chloride : 10 mol %) emulsion. As a hardener, 10 ml of a 5% methanol solution of triethylenephosphonamide was added thereto. The mixture thus obtained was coated on a polyethylene-coated sheet and dried to obtain light-sensitive silver halide photographic materials. Then, after these samples were processed in the same manner as in Example 1, the measurement was carried out in the same manner as in Example 1, except that the dye density only after the 50 hour exposure to the irradiation by the xenon fade-o-meter was measured, as an after-exposure density, by using blue light, to obtain the results in Table 2-2.

Table 2 - 1

| No. | Couplers Amount (g) | Compounds Amount (g) | | High B.P. Solvent Amount (cc) | | Low B.P. Solvent Amount (cc) | |
|---|---|---|---|---|---|---|---|
| 1 | (Y-3) 61 | — | — | DBP | 61 | EA | 120 |
| 2 | " " | (8) | 22 | " | " | " | " |
| 3 | " " | (13) | " | " | " | " | " |
| 4 | " " | (18) | " | " | " | " | " |
| 5 | (Y-5) 76 | — | — | TCP | 76 | " | " |
| 6 | " " | (15) | 23 | " | " | " | " |
| 7 | " " | (19) | " | " | " | " | " |
| 8 | " " | (26) | " | " | " | " | " |

Table 2 - 2

| Samples | Color-fading ratio | Y-Stain Increase ratio |
|---|---|---|
| 1 | 58 | 138 |
| 2 | 67 | 113 |
| 3 | 71 | 121 |
| 4 | 70 | 110 |
| 5 | 90 | 126 |
| 6 | 93 | 117 |
| 7 | 95 | 119 |
| 8 | 94 | 115 |
| Controls | | |
| 1 | 58 | 129 |
| 2 | 29 | 140 |
| 3 | 32 | 135 |
| 4 | 91 | 123 |
| 5 | 75 | 130 |
| 6 | 63 | 126 |

In the above table, Controls 1-6 were used in such combination of a coupler with a color-fading inhibitor shown in Table 2-3.

Table 2 - 3

| Controls | Couplers Amount (g) | Conventional Inhibitors Amount (g) | |
|---|---|---|---|
| 1 | (Y-3) 61 | (I) | 18 |
| 2 | " " | (II) | " |
| 3 | " " | (III) | " |
| 4 | (Y-5) 76 | (I) | " |
| 5 | " " | (II) | " |
| 6 | " " | (III) | " |

As obvious from the results shown in Table 2-2, the compounds of this invention were proved to be excellent in the effect of inhibiting the colored-fading of a yellow dye image, as well, in comparison with the fact that the conventionally known compounds had either little color-fading inhibiting effect or rather colorfading accelerating effect. Further, the compounds of this invention were proved to inhibit effectively the Y-Stain of the unexposed portion.

EXAMPLE 3

46 g of a cyan coupler (C-1), 200 mg of 2,5-dit-octylhydroquinone and 12 g of the compound shown in Table 3 were dissolved into a mixture of 40 g of dibutylphthalate and 120 g ethyl acetate. The resulted solution was added to 500 cc of an aqueous 5% gelatin solution containing sodium dodecylbenzenesulfonate. After dispersed by a homogenizer, the obtained dispersion was added to 1,000 cc of a red light sensitive silver chlorobromide (Silver chloride : 20 mol %) emulsion. As a hardner, 20 ml of an aqueous 4% 2,4 dichloro-6-hydroxy-s-triazine sodium salt was added thereto. Then, the resulted mixture was coated on a polyethylene-coated sheet and dried to prepare a light sensitive silver halide photographic material. Next, the same process as mentioned above, except that 45 g of a cyan coupler (C-3) was used instead of 46 g of a cyan coupler (C-1), was carried out. The samples were processed in the same manner as in Example 1 and the measurement was carried out in the same manner as in Example 1, except that the dye density only after the 150 hour exposure to the irradiation by the xenon fade-o-meter was measured an after exposure density by using red light to obtain the results in Table 3.

Table 3

| Samples | Color-fading Inhibitors Amount (g) | | Color-fading ratio Cyan Couplers | |
|---|---|---|---|---|
| | | | C - 1 | C - 3 |
| 1 | — | — | 86 | 92 |
| 2 | Compound (4) | 12 g | 93 | 91 |
| 3 | " (13) | " | 90 | 93 |
| 4 | " (18) | " | 94 | 92 |
| 6 | Conventional Inhibitor (I) | " | 87 | 89 |
| 7 | " (III) | " | 89 | 89 |

EXAMPLE 4

Onto a polyethylene-coated paper sheet, the following layers were formed successively in the order from the support side to prepare a silver halide color photographic material (Sample 1):

The First Layer;

A blue light sensitive silver halide emulsion layer, comprising a silver chlorobromide emulsion containing 10 mol % of silver chloride which emulsion contained 400 g of gelatin based on one mole of silver halide, was sensitized with 2.5 × 10⁻⁴ mole of a sensitizing dye having the following structure:

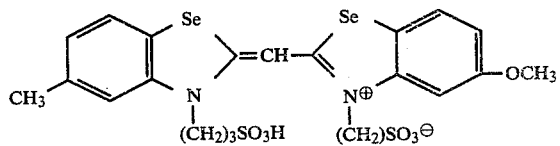

based on one mole of silver halide, contained 2 × 10⁻¹ mole of the yellow coupler (Y-6) based on one mole of silver halide dissolved and dispersed in dibutylphthalate, and was coated so that the layer contained a silver amount of 400 mg/m².

The Second Layer;

A gelatin layer coated to have the dry thickness of one micron.

The Third Layer;

A green light sensitive silver halide emulsion layer, comprising a silver chlorobromide emulsion containing 40 mol % of silver chloride which emulsion contained 500 g of gelatin based on one mole of silver halide, was sensitized with $2.5 \times 10^{-4}$ mole of the sensitizing dye having the following structure:

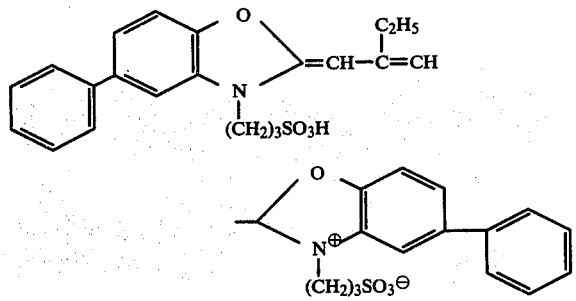

based on one mole of silver halide, contained $2 \times 10^{-1}$ mole magenta coupler (M-14) based on one mole of silver halide dissolved and dispersed in tricresylphosphate and was coated so that the layer contained a silver amount of 400 mg/m².

The Fourth Layer;

A gelatin layer having one micron thickness containing 30 mg/m² of di-t-octylhydroquinone dissolved and dispersed into dibutylphthalate.

The Fifth Layer;

A red light sensitive silver halide emulsion layer comprising a silver chlorobromide emulsion containing 20 mol % of silver chloride which emulsion contained 500 g of gelatin based on one mole of silver halide, was sensitized with $2.5 \times 10^{-4}$ mole of the sensitizing dye having the following structure:

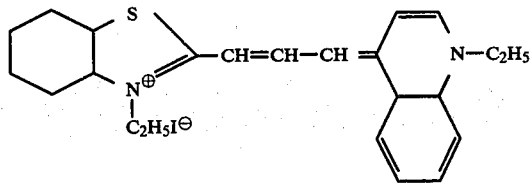

based on one mole of silver halide, contained $2 \times 10^{-1}$ mole of the cyan coupler (C-3) based on one mole of silver halide dissolved and dispersed into tricresyl phosphate, and was coated so that the layer contained a silver amount of 500 mg/m².

The Sixth Layer;

A protective layer being a gelatin layer coated to have the dry thickness of one micron.

The above-layering was repeated to obtain sample (2) except for the following:

(The silver halide emulsions used for the respective light-sensitive layers (The First, Third and Fifth Layers) were regulated in such process as disclosed in Japanese Patent Publication No. 7,772/71. The respective emulsions were subjected to chemical sensitization with sodium thiosulfate pentahydrate and incorporated with 4-hydroxy-6-methyl-1·3·3$_a$·7-tetraazaindene as a stabilizer, bis(vinylsulfonylmethyl) ether as a hardner and saponin as a coating aid.

Then, in the respective First, Third and Fifth light sensitive layers, the respective couplers were incorporated with exemplified compounds (13) of this invention in an amount of 30 wt % based on the respective couplers and then the mixtures were dispersed to the layers.)

Further, in Sample 2, the Fourth layer thereof was incorporated with a gelatin solution containing 2-(2'-hydroxy-3',5',-di-t-butylphenyl)benzotriazole dissolved and dispersed in tricresylphosphate as an ultraviolet absorbing agent, the gelatin solution being used in such an amount that the amount of said ultraviolet absorbing agent might be 0.7 g/m² to obtain Sample 3.

Furthermore, those obtained by using in preparation of Sample 2 the conventionally known Compounds (II) and (III) instead of the compound of this invention but in the same amount as that of the latter were respectively shown as Samples 4 and 5. And those as obtained by using in preparation of Sample 3 the conventionally known compounds (II) and (III) instead of the compound of this invention but in the same amount as that of the latter were respectively shown as Samples 6 and 7. Sample 8 was prepared according to the same method as for sample 1 except that compound (4) of this invention was incorporated in the magenta coupler containing layer in an amount of 30 wt % based on the magenta coupler weight while samples 9 and 10 were prepared according to the same method for sample 8 except that known compounds (II) and (III) were respectively employed in place of compound (4) in the same amount.

The samples as prepared above were exposed to light through wedges to blue, green and red lights respectively according to a sensitometry process, processed in the same manner as in Example 1, and exposed to the irradiation by the xenon fade-o-meter for 100 hours. The results of measurement of the respective dye densities were shown in Table 4.

Table 4

| Sample | Color-fading ratio | | | Y-Stain Increase ratio |
| --- | --- | --- | --- | --- |
| | Yellow | Mazenta | Cyan | |
| 1 | 91 | 73 | 93 | 450 |
| 2 | 93 | 95 | 94 | 150 |
| 3 | 94 | 97 | 95 | 130 |
| 4 | 58 | 81 | 92 | 280 |
| 5 | 62 | 82 | 92 | 290 |
| 6 | 66 | 87 | 93 | 204 |
| 7 | 70 | 89 | 93 | 216 |
| 8 | 91 | 94 | 93 | 170 |
| 9 | 90 | 80 | 92 | 270 |
| 10 | 91 | 81 | 93 | 280 |

As obvious from the results of Table 4, the compounds of the present invention were proved to be very excellent color-fading inhibitors having not only an excellent effect in color-fading inhibition concerning a mazenta image but also a good effect in color-fading inhibition concerning yellow and cyan dye images.

Example 5

12 g of compound (13) was dissolved into 11 g of dibutylphthalate and 30 g of ethyl acetate. The solution was incorporated into 120 cc of an aqueous 5% gelatin solution containing sodium dodecylbenzene sulfonate. After dispersed by a homogenizer, the resulted dispersion was incorporated into 300 cc of a green lightsensitive silver chlorobromide emulsion (silver chloride: 30 mol %). The resulting emulsion was coated on a polyethylene-coated paper sheet and dried to obtain a silver halide photographic material.

The silver halide photographic material was exposed to light through wedges according to a sensitometry process and processed at the temperature of 24° C. in the following order:

| Steps | Time of Processing |
| --- | --- |
| Primary Developing | 5 min. |
| Water-washing | 4 min. |
| Exposing to light entirely | |
| Color-developing | 3 min. |
| Water-washing | 4 min. |
| Bleaching | 4 min. |
| Fixing | 4 min. |
| Water-washing | 10 min. |

The primary developing solution, the color developing solution, the bleaching solution and the fixing solution were used respectively in the following compositions:

| Bleaching Solution Composition | |
| --- | --- |
| Anhydrous sodium iodide | 43.0 g |
| Potassium Ferricyanide | 165.0 g |
| Borax ($Na_2B_4O_7 \cdot 10H_2O$) | 1.2 g |
| Water | To make the total 1 l. |
| Fixer Composition | |
| Sodium thiosulfate (pentahydrate) | 200 g |
| Anhydrous sodium sulfate | 100 g |
| Anhydrous 2 sodium phosphate | 15.0 g |
| Water | To make the total 1 l. |

The color-fading ratio and the Y-stain increase ratio in the unexposed portion were measured in the same manner as in Example 1, except that the resultant color photographic material was exposed to the irradiation by the xenon face-o-meter for only 100 hours. As a control, the case of using conventionally known compound (III) instead of the compound of this invention but in the same amount therewith was shown. And the case "Blank" was that of not using compound (13). These results were shown in Table 5.

Table 5

| Samples | Color-fading Inhibitor | Color-fading ratio | Y-Stain Increase ratio |
| --- | --- | --- | --- |
| 1 | Blank | 65 | 480 |
| 2 | Compound (13) | 92 | 125 |
| 3 | Conventional Inhibitor (III) | 87 | 165 |

The results of Table 5 show that the compound of the present invention has an excellent effect in color-fading inhibition, while inhibiting Y-stain, even in the case that a coupler is not contained in the silver halide photographic material.

What we claim is:

1. A color photosensitive material comprising a support and a silver halide photosensitive layer, said material containing a compound represented by the formula:

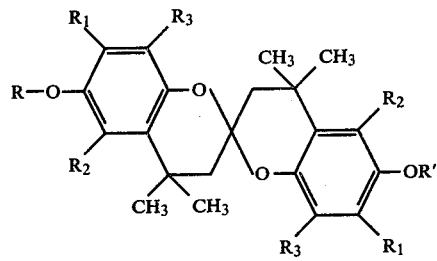

wherein $R_1$ represents an alkyl, alkenyl, aryl, alkoxyl, alkenoxyl or aryloxyl group; $R_2$ and $R_3$ individually represent hydrogen, halogen, or an alkyl, alkenyl, or alkoxyl group; R represents an alkyl, alkenyl, cycloalkyl, aryl or heterocyclic group selected from imidazolyl, furyl, pyridyl, or thiazolyl or a $R_6CO—$, $R_7SO_2—$ or $R_8NHCO—$ group; R' is hydrogen or an $R_6CO—$, $R_7SO_2—$, or $R_8NHCO—$ group; in which $R_6$, $R_7$ and $R_8$ individually represent an alkyl, alkenyl, cycloalkyl, aryl or heterocyclic group selected from imidazolyl, furyl, pyridyl and thiazolyl; and, when R' represents the $R_6CO—$, $R_7SO_2—$ or $R_8NHCO$-group, R can be either the same as or different from R'.

2. The color photosensitive material according to claim 1 wherein the photosensitive layer contains the compound.

3. The color photosensitive material according to claim 1 wherein the photosensitive material further comprises a layer adjacent to the photosensitive layer, said adjacent layer containing the compound.

4. The color photosensitive material according to claim 1 wherein R is alkyl, alkenyl, or cycloalkyl, the alkyl and alkenyl for R having 1–32 carbon atoms, R' is hydrogen, $R_6CO—$ or $R_7SO_2—$, $R_6$ is alkyl or an aryl group, $R_7$ is an aryl group, $R_1$ is methyl or tolyl, $R_2$ and $R_3$ is hydrogen.

5. A color photosensitive material comprising a support, a cyan-coupler containing silver halide photosensitive emulsion layer, a magenta coupler containing silver halide photosensitive emulsion layer, and a yellow coupler containing silver halide photosensitive emulsion layer, said material containing a compound represented by the formula:

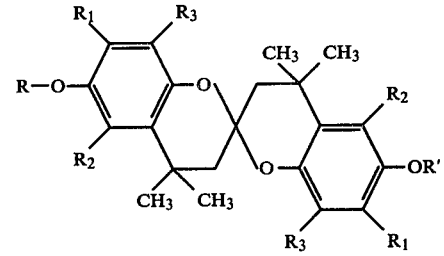

wherein $R_1$ represents an alkyl, alkenyl, aryl, alkoxyl, alkenoxyl or aryloxyl group; $R_2$ and $R_3$ individually represent hydrogen, halogen, or an alkyl, alkenyl, or alkoxyl group; R represents an alkyl, alkenyl, cycloalkyl, aryl or heterocyclic group selected from imidazolyl, furyl, pyridyl, and thiazolyl or, a $R_6CO—$, $R_7SO_2—$ or $R_8NHCO—$ group; R' is hydrogen or an $R_6CO—$, $R_7SO_2—$, or $R_8NHCO—$ group; in which $R_6$, $R_7$ and $R_8$ individually represent an alkyl, alkenyl, cycloalkyl, aryl or heterocyclic group selected from imidazolyl, furyl, pyridyl, and thiazolyl and, when R' represents the $R_6CO-$, $R_7SO_2-$ or $R_8NHCO$-group, R can be either the same as or different from R'.

6. The color photosensitive material according to claim 5 wherein at least one of the three emulsion layers contains the compound.

7. The color photosensitive material according to claim 6 wherein at least one of the yellow coupler containing silver halide photosensitive emulsion layer and the cyan coupler containing silver halide photosensitive emulsion layer contains the compound.

8. The color photosensitive material according to claim 7 wherein R is alkyl having 1–18 carbon atoms, R' is $R_6CO-$ in which $R_6$ is alkyl of 1–18 carbon atoms or phenyl substituted with alkyl of 1–18 carbon atoms, $R_1$ is methyl, $R_2$ and $R_3$ is hydrogen.

9. The color photosensitive material according to claim 6 wherein the magenta coupler containing silver halide photosensitive emulsion layer contains the compound.

10. The color photosensitive material according to claim 9 wherein said magenta coupler is a 5-pyrazolone coupler.

11. The color photosensitive material according to claim 10 wherein R is alkyl of 1–18 carbon atoms, R' is hydrogen or $R_6CO-$ in which $R_6$ is alkyl of 1–18 carbon atoms or phenyl substituted with alkyl of 1–18 carbon atoms, $R_2$ and $R_3$ are hydrogen and $R_1$ is methyl.

12. The color photosensitive material according to claim 11 wherein the magenta coupler is a 3-anilino-5-pyrazolone coupler.

13. The color photosensitive material according to claim 12 wherein R' is $R_6CO-$.

* * * * *